US012078632B2

(12) United States Patent
van den Driesche et al.

(10) Patent No.: US 12,078,632 B2
(45) Date of Patent: Sep. 3, 2024

(54) PROCESS FOR CARRYING OUT AN ALLERGY TEST, PROCESS FOR DETERMINING DEGRANULATION IN CELLS, DEVICE FOR CARRYING OUT AN ALLERGY TEST AND MICROFLUIDIC CHIP

(71) Applicants: Universität Bremen, Bremen (DE); Medizinische Universität Wien, Vienna (AT)

(72) Inventors: Sander van den Driesche, Bremen (DE); Michael Vellekoop, Bremen (DE); Claas Falldorf, Bremen (DE); Christine Hafner, Vienna (AT); Heimo Breiteneder, Vienna (AT)

(73) Assignees: UNIVERSITÄT BREMEN, Bremen (DE); MEDIZINISCHE UNIVERSITÄT WIEN, Vienna (AT)

( * ) Notice: Subject to any disclaimer, the term of this patent is extended or adjusted under 35 U.S.C. 154(b) by 1405 days.

(21) Appl. No.: 16/333,404

(22) PCT Filed: Sep. 14, 2017

(86) PCT No.: PCT/EP2017/073144
§ 371 (c)(1),
(2) Date: Mar. 14, 2019

(87) PCT Pub. No.: WO2018/050749
PCT Pub. Date: Mar. 22, 2018

(65) Prior Publication Data
US 2019/0250146 A1 Aug. 15, 2019

(30) Foreign Application Priority Data
Sep. 15, 2016 (DE) ...................... 10 2016 117 421.1

(51) Int. Cl.
*G01N 33/50* (2006.01)
*B01L 3/00* (2006.01)
*G02B 21/08* (2006.01)

(52) U.S. Cl.
CPC .... *G01N 33/5047* (2013.01); *B01L 3/502761* (2013.01); *G01N 33/5076* (2013.01); *G02B 21/086* (2013.01); *G01N 2800/24* (2013.01)

(58) Field of Classification Search
CPC .......... G01N 33/56972; G01N 33/5076; B01L 3/502761
See application file for complete search history.

(56) References Cited

U.S. PATENT DOCUMENTS

2015/0018226 A1\* 1/2015 Hansen ................... G01N 1/34
435/6.12
2016/0131882 A1 5/2016 Wallace

FOREIGN PATENT DOCUMENTS

DE  10 2008 018 170 B4  5/2010
DE  10 2014 200 911 A1  4/2015
(Continued)

OTHER PUBLICATIONS

R. Hastie. The Antigen-Induced Degranulation of Basophil Leucocytes from Atopic Subjects, Studied by Phase-Contrast Microscopy. Clin Exp Immunol. 8: 45-61 (1971).\*
(Continued)

*Primary Examiner* — Gailene Gabel
(74) *Attorney, Agent, or Firm* — McGlew and Tuttle, P.C.

(57) ABSTRACT

A process for carrying out an allergy test is based on a blood sample being taken. The blood sample is contacted in vitro with at least one allergen. At least one allergic reaction or the absence of the at least one allergic reaction is observed via a microscope (11) directly and/or optically. To make it possible to carry out an allergy test with a higher validity and/or better accuracy, a position of granules is observed via (Continued)

the microscope (11). The granules are observed in different planes or horizontal planes.

20 Claims, 3 Drawing Sheets

(56) References Cited

FOREIGN PATENT DOCUMENTS

| DE | 102014205535 A1 | 10/2015 |
|---|---|---|
| WO | 93/25904 A1 | 12/1993 |
| WO | 2013/083815 A1 | 6/2013 |
| WO | 2014/019 603 A1 | 2/2014 |

OTHER PUBLICATIONS

Depeursinge et al. Cell Biology explored with Digital Holographic Microscopy. Biomedical Optics. BMD58: BD 6880110: 1-4 (Jan. 1, 2008).*

Evans et al. Holographic microscopy and microfluidics platform for measuring wall stress and 3D flow over surfaces textured by micropillars. Scientific Reports 6:28753. DOI:10.1038/srep28753. 1-12 (Jun. 29, 2016).*

Huang et al. Optoelectronic tweezers integrated with lensfree holographic microscopy for wide-field interactive cell and particle manipulation. Lab Chip 13: 2278-2284 (2013).*

H Bocanegra Evans et al: "Holographic microscopy and microfluidics platform for measuring wall stress and 3D flow over surfaces textured by micro-pillars". Scientific Reports. Bd. 6. Nr. 1. 29. Jun. 2016 (Jun. 29, 2016). XP055755512.

Zoltan Gorocs et al: "On-Chip Biomedical Imaging". IEEE Reviews in Biomedical Engineering. IEEE. USA. Bd. 6. 1. Jan. 1, 2013 (Jan. 1, 2013). pp. 29-46. XP011499449. ISSN: 1937-3333. DOI: 10.1109/RBME.2012.2215847.

Kuo-Wei Huang et al: "Optoelectronic tweezers integrated with lensfree holographic microscopy for wide-field interactive cell and particle manipulation on a chip", Lab on a Chip, Bd. 13, Nr. 12, Jan. 1, 2013 (Jan. 1, 2013), p. 2278, XP055250778, DOI: 10.1039/c3lc50168j.

M Haapalainen et al: "Characterizing electrokinetic mobility of microparticles using in-line holographic microscopy", Photonics Letters of Poland, Bd. 3, Nr. 2, Jun. 30, 2011 (Jun. 30, 2011), XP055756060, DOI: 10.4302/plp.2011.2.14.

J Voldman: "Dielectrophoretic Traps for Cell Manipulation" In: "BioMEMS and Biomedical Nanotechnology", Jan. 1, 2006 (Jan. 1, 2006), Springer US, Boston, MA, XP055040051, ISBN: 978-0-38-725566-8 pp. 159-186, DOI: 10.1007/978-0-387-25845-4 8.

Shu-Hsien Liao et al: "A capillary dielectrophoretic chip for real-time blood cell separation from a drop of whole blood", Biomicrofluidics, Bd. 7, Nr. 2, 1. Mar. 1, 2013 (Mar. 1, 2013), p. 024110, XP055755804, DOI: 10.1063/1.4802269.

C Depeursinge et al: "Cell Biology Explored with Digital Holographic Microscopy", Biomedical Optics, Bd. 6880110, Jan. 1, 2008 (Jan. 1, 2008), p. BMD58, XP055428344, DOI: 10.1364/BIOMED.2008.BMD58.

R Hastie: "The antigen-induced degranulation of basophil leucocytes from atopic subjects, studied by phase-contrast microscopy", Clinical and experimental immunology, vol. 8 Jan. 1, 1971 (Jan. 1, 1971), pp. 45-61, XP055429915, Retrieved from the Internet: URL:https://www.ncbi.nlm.nih.gov/pmc/articles/PMC1712904/pdf/clinexpimmunol00374-0053.pdf.

L. A. S. Carmo et al: "CD63 is tightly associated with intracellular, secretory events chaperoning piecemeal degranulation and compound exocytosis in human eosinophils", Journal of Leukocyte Biology, vol. 100, No. 2, Mar. 10, 2016 (Mar. 10, 2016), pp. 391-401.

M Kurosawa et al: "Phase-contrast microscopic studies using cinematographic techniques and scanning electron microscopy on IgE-mediated degranulation of cultured human mast cells", Clinical & Experimental Allergy, vol. 28, No. 8, Aug. 1, 1998 (Aug. 1, 1998), pp. 1007-1012.

R. Sher et al: "Eosinophil degranulation: Monitoring by interference contrast microscopy", Inflammation., vol. 5, No. 1, Mar. 1, 1981 (Mar. 1, 1981), pp. 37-53.

* cited by examiner

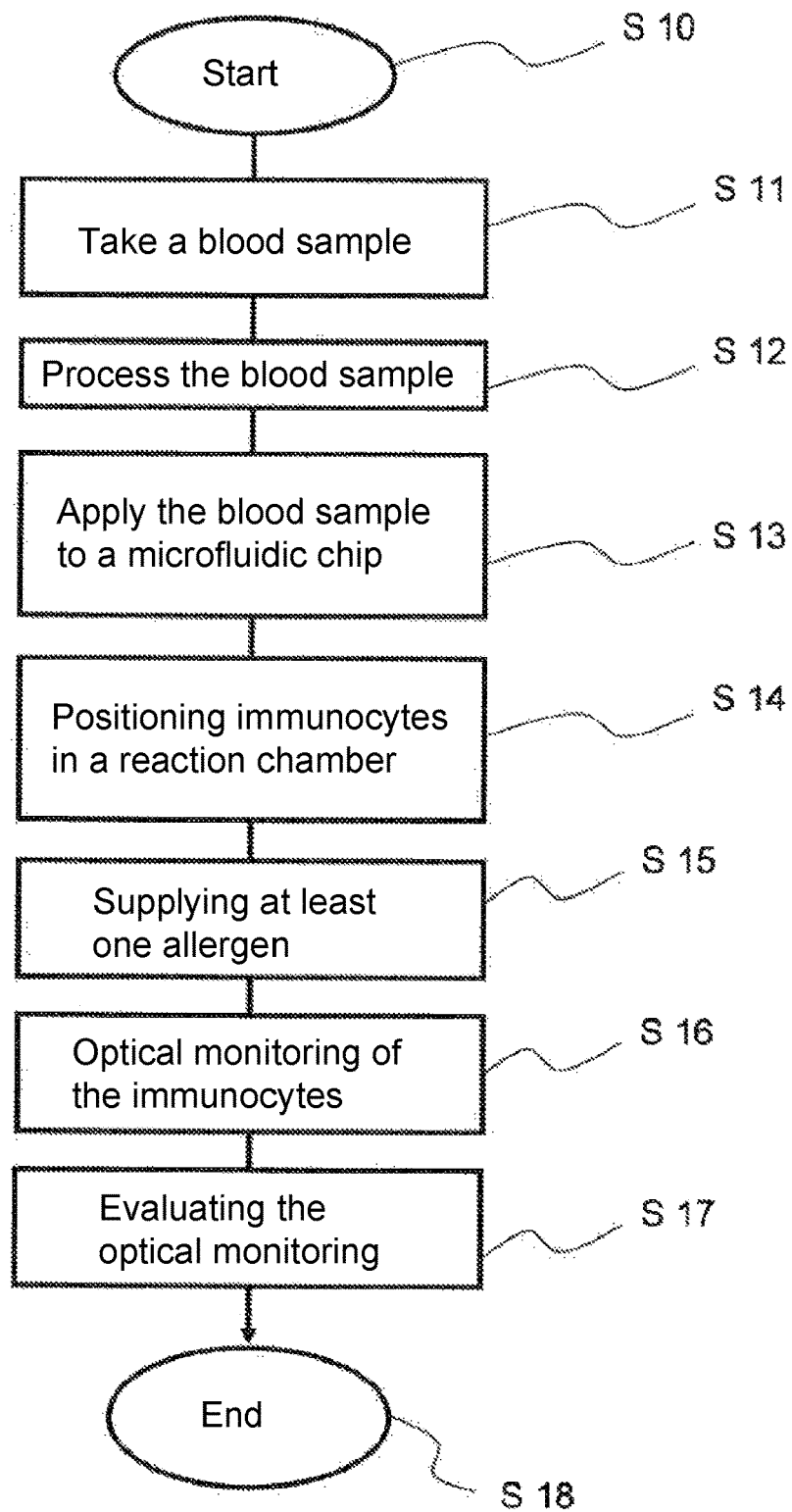

PROCESS FOR CARRYING OUT AN ALLERGY TEST, PROCESS FOR DETERMINING DEGRANULATION IN CELLS, DEVICE FOR CARRYING OUT AN ALLERGY TEST AND MICROFLUIDIC CHIP

CROSS REFERENCE TO RELATED APPLICATIONS

This application is a United States National Phase Application of International Application, PCT/EP2017/073144, filed Sep. 14, 2017, and claims the benefit of priority under 35 U.S.C. § 119 of German Application 10 2016 117 421.1, filed Sep. 15, 2016, the entire contents of which are incorporated herein by reference.

TECHNICAL FIELD

The present invention pertains to a process for carrying out an allergy test, in which a blood sample is taken, in which the blood sample is contacted in vitro with at least one allergen, and in which at least one allergic reaction or the absence of the at least one allergic reaction is observed by means of a microscope directly and/or optically. The present invention pertains, furthermore, to a process for determining degranulation in cells, in which a blood sample is taken, and in which the blood sample is contacted in vitro with at least one reaction partner. The present invention pertains, furthermore, to a device for carrying out an allergy test with a microscope and with an at least partially transparent microfluidic chip for the direct and/or optical observation of an allergic reaction or for the observation of the absence of an allergic reaction, as well as to a microfluidic chip.

TECHNICAL BACKGROUND

The term blood sample is used within the framework of the present application as a synonym for a direct blood sample or for a serum from a direct blood sample, which was mixed or brought into contact with cells of special cell lines. The special cell lines may be, above all, humanized cells, especially rat cells and/or guinea pig cells.

Corresponding processes for carrying out an allergy test are known as blood tests, in which an immunoglobulin-antibody level, especially an immunoglobulin-E level, is determined. Cells of endogenous immune defense contain granules containing, for example, histamine, which they release on activation. An activation process takes place, in particular, via the immunoglobulin E (IgE), which is bound to the cell membrane of an immunocyte during sensitization. In case of an existing sensitization to a certain allergen, a degranulation process may be triggered, during which granules are released from the immunocyte. The degranulation or the release of the granules from the immunocyte represents here an initiation of an allergic inflammatory reaction.

It is disadvantageous in this connection that the determination of an allergy is based on the antibody-based detection of IgE. IgE is a marker for an allergic sensitization, an allergy, an inflammation and/or certain hematological diseases. This means that an allergy does not necessarily have to be present in case of an antibody-based detection of an allergy on the basis of the analysis of IgE antibodies, even if the test itself is positive. As a result, there is a risk of a large number of misinterpretations of the test results. Thus, the percentage of false positive interpretations of the test results obtained for determining an allergy may, for example, be in the range of 50% to 60%. The percentage of false negative test results may be in the range of 15% to 20%.

To identify false test results or to confirm an allergy, it is known that a so-called challenge test can be carried out. For example, an oral challenge test may be carried out. It is, however, disadvantageous in this case that this may be very unpleasant for the particular person being tested or for the patient due to the allergic reaction being challenged. In particular, there is a risk of a life-threatening anaphylactic shock in case of a challenge test.

It is disadvantageous, moreover, that an allergy test based on an antibody-based detection of IgE is an indirect method. The detection of the IgE molecules determined in a blood sample is carried out, in particular, by means of enzyme-labeled antibodies against IgE. A corresponding complex can be detected with a second development reaction, especially by means of fluorescence. An allergic reaction can consequently only be detected indirectly by means of indirect allergy indicators, especially IgE antibodies or fluorescence.

SUMMARY

A basic object of the present invention is therefore to further improve a process, a device and a microfluidic chip of the above-mentioned class such that an allergy test can be carried out with increased validity and/or better accuracy. In particular, a more rapid and/or more cost-effective allergy test shall be made available. Furthermore, at least one alternative embodiment shall be provided.

The basic object of the present invention is accomplished with a process of the class mentioned in the introduction for carrying out an allergy test, in which the position of granules is observed by means of the microscope, wherein the granules are observed in different planes or in different horizontal planes. To accomplish the object, provisions are made in the process for determining degranulation in cells for the direct and/or optical observation of degranulation or of the absence of degranulation by means of a microscope. Furthermore, the object is accomplished with a device for carrying out an allergy test of the above-described class such that the microscope is configured to generate a holographic image.

It is advantageous in this connection that an allergic reaction can be determined directly. In particular, degranulation of preferably defined or predefined immunocytes can be observed directly. Degranulation can be considered in this connection to be a relevant parameter for determining an allergic reaction. Based on a visualization of a degranulation process, a direct method can thus be provided for determining an allergy. This makes possible an improved and more reliable determination of allergies. As a result, it is possible to dispense with indirect methods for determining an allergy. In addition, a direct and/or optical observation of an allergic reaction can make it possible to obtain a more accurate, more rapid and/or more cost-effective allergy test.

A direct and/or optical observation is preferably defined within the framework of the present invention as a determination, monitoring, detection and/or measurement. A direct and/or optical observation is defined, in particular, as a recording and/or analysis of data and/or images. A direct and/or optical observation may be configured as a quantitative microscopic examination, especially a quantitative phase-contrast microscopic examination. Contrary to an indirect determination of an allergic reaction by means of a marker or indirect allergy indicator, an allergic reaction can be determined, observed and/or measured directly by means of the present invention. A more complicated analysis of a marker or of an indirect allergy indicator can thus be dispensed with in case of a direct observation, determination, monitoring, detection and/or measurement of an allergic reaction. As a result, an allergy can be identified more accurately, with higher reliability, more rapidly and/or in a more cost-effective manner.

According to another embodiment, degranulation of immunocytes of the blood sample, especially of defined and/or predefined immunocytes of the blood sample, is observed with the microscope especially quantitatively in case of an allergic reaction. The immunocytes are part of the blood sample here. The blood sample may be a direct blood sample or a serum from a direct blood sample, which was mixed or brought into contact with cells of special cell lines. The immunocytes are preferably granulocytes, basophilic cells, basophilic granulocytes and/or mast cells. In particular, granules of cells are observed, monitored, measured and/or recorded. In particular, a path of motion of the granules is observed, measured and/or recorded over a predefined time. It is preferably observed whether granules of a cell leave the cell or are released from the cell within a predefined time after contacting the cell with the at least one allergen Immunocytes are preferably defined within the framework of the present invention as cell types of a blood sample that may potentially exhibit a sensitization for an allergic reaction. Based on the direct and/or optical observation of the immunocytes on contacting the cells with the at least one allergen, the absence of degranulation can be classified as a non-allergic reaction. If degranulation takes place, this may be classified as an allergic reaction. It is thus possible to determine directly and/or in real time based on the observation of the motion of the granules whether or not an allergic sensitization or allergy is present.

According to a variant, the blood sample is processed in order to increase the percentage of immunocytes after the blood sample was taken and before contacting it with the at least one allergen. The blood sample may be taken in a manner known per se. The blood sample of a person or of a patient is taken, for example, by means of a needle or a syringe. A relatively small quantity of blood may suffice as a blood sample. A quantity of blood less than 100 mL, less than 10 mL or less than 1 mL is preferably sufficient. Additives may be added to the blood sample within the framework of the processing of the blood sample. The additives may be, for example, sodium citrate and/or heparin. Based on a suitable processing of the blood sample, clotting of the blood can be avoided or delayed. In particular, the percentage of immunocytes in the blood sample is increased. The percentage of immunocytes in the blood sample may be increased, for example, to more than 5%, more than 10%, more than 20% or higher.

The percentage of red blood cells is preferably reduced within the framework of the processing of the blood sample. The reduction or removal of red blood cells from the blood sample may be carried out by means of usual, especially chemical, electric and/or mechanical methods. In particular, the percentage of the white blood cells different from the immunocytes to be tested is reduced. The percentage of the immunocytes to the tested, especially granulocytes, basophilic cells, basophilic granulocytes and/or mast cells, may be increased by removing white blood cells different from these. Basophilic cells may be isolated, in particular, by removing all other white blood cells. Processes, methods or techniques that are known per se and/or usual may be used for this purpose. Based on the processing of the blood sample, it is possible to increase the percentage of immunocytes to be tested in the blood sample to more than 5%, to more than 10%, to more than 20% or higher. It is possible, in particular, to reach a percentage in a range of 10% to 20% or higher. To determine the degranulation of the cells being tested and/or to observe an allergic reaction, it is consequently unnecessary to completely isolate the cells to be tested from all other components of the blood sample. The processed blood sample may be suspended in a suitable medium in order to improve the shelf life, especially for a time of several hours.

According to another embodiment, a microfluidic chip is used for contacting the blood sample with the at least one allergen. Even a relatively small quantity of blood sample, especially in the range of one drop or several drops, may be provided for a test by means of a microfluidic chip. A microfluidic chip may have a microchannel or a plurality of microchannels. Furthermore, a microfluidic chip may be composed of a plurality of layers. A layer having at least one microchannel and/or at least one reaction chamber may be formed from silicon. An upper and/or lower cover layer or carrier layer may be formed from a transparent material, especially glass or plastic. A silicon layer is preferably arranged between two transparent layers, especially glass layers. In particular, immunocytes of the blood sample are arranged in at least one reaction chamber of the chip. The microfluidic chip may have a plurality of reaction chambers for receiving immunocytes of the blood sample. The plurality of reaction chambers may be separated from one another and/or connected to one another by means of one or more microchannels. The reaction chamber and/or at least one reference chamber of the microfluidic chip preferably has an at least partially transparent configuration. The at least one reaction chamber and/or the at least one reference chamber may have a transparent configuration and/or be covered on at least one side. Transparency is defined, in particular, as a transparency in relation to electromagnetic waves and/or light of different wavelengths.

At least one allergen is preferably guided into the at least one reaction chamber. At least one allergen is added especially after a plurality of immunocytes have been guided into the at least one reaction chamber. A predefined, single allergen may now be guided into a certain, predefined reaction chamber. As an alternative, a plurality of allergens, specially a defined number of predefined types of allergens, may be guided into the reaction chamber. The at least one allergen is especially guided both into the at least one reaction chamber containing the immunocytes and into a reference chamber containing no immunocytes. The reference chamber can likewise be observed directly and/or optically by means of the microscope. The observation of the at least one reaction chamber and of the associated reference chamber is carried out, in particular, together and/or simultaneously. The observation of the reference chamber without immunocytes may improve the analysis and/or the quality of the result of the observation compared to the observation of the associated reaction chamber containing the immunocytes. In particular, a quantitative phase contrast is measured by interferometry by means of the observation of the at least one reaction chamber and of the associated reference chamber. A reference chamber is preferably associated with each reaction chamber. Thus, an equal number of reference chambers is present in case of a microfluidic chip having a plurality of reaction chambers. The immunocytes, on the one hand, and the at least one allergen, on the other hand, may be guided into the at least one reaction chamber and/or into the at least one reference chamber by means of the same microchannel or by means of different microchannels.

The immunocytes of the blood sample are preferably arranged or positioned on or in the microfluidic chip by means of a suitable process and/or a suitable device. In particular, immunocytes of the blood sample are arranged on or in the microfluidic chip by means of a microfluidic cell trap, electrophoresis, dielectrophoresis and/or mechanical methods. An inhomogeneous electrical field may be used in dielectrophoresis to move, separate, arrange and/or position cells or immunocytes. Based on the inhomogeneous electrical field, a dipole moment can be induced in the cells, and this dipole moment will then interact with the electrical field applied. The cells are subject in the process to a force and move, depending on the field and the dipole moment, into areas of high or low field intensity. The action of the force may be proportional to the volume of the cells. The cells, especially the immunocytes, can thus be captured in a type of "field cage" Immunocytes are positioned and/or held, in particular, in at least one reaction chamber by means of electrophoresis and/or dielectrophoresis Immunocytes may preferably be divided and arranged in a plurality of reaction chambers by means of dielectrophoresis. Based on the separation of the immunocytes into a plurality of reaction chambers, different allergens can be contacted simultaneously with immunocytes in mutually separate reaction chambers. Depending on the selected number of reaction chambers and/or allergens used, it is thus possible to test a plurality of allergic sensitizations or allergies simultaneously.

At least one reference chamber is preferably provided without or free from immunocytes by means of electrophoresis and/or dielectrophoresis. It is thus possible by means of electrophoresis and/or dielectrophoresis to make available a reference chamber in which no immunocytes are present. The immunocytes can be guided within the microfluidic chip by means of electrophoresis and/or dielectrophoresis such that the area of the reference chamber becomes or remains cell-free. The reference chamber free from immunocytes can be optically superimposed in this manner with the at least one reaction chamber containing immunocytes. As a result, a quantitative phase contrast of the immunocytes can be measured by interferometry. The light, which passes at least partially through the reaction chamber, and the light passing at least partially through the reference chamber, are superimposed, in particular. The superimposed light may have an essentially or approximately identical path, especially through the microfluidic chip. As a result, sensitivity to external mechanical effects can be reduced. In particular, the need for a complicated and/or costly insulation against vibration may be eliminated.

According to a variant, the position and/or a change in the position of granules of the immunocytes are observed directly and/or optically by means of the microscope. Granules are, in particular, granular inclusions visible by means of the microscope in biological cells, especially immunocytes. The release of granules from the cells, especially immunocytes, is called degranulation. Granules are observed, in particular, in different planes or horizontal planes. A plurality of immunocytes may be present in the at least one reaction chamber. The immunocytes may be arranged at different levels or in different horizontal planes. To make it possible to observe an allergic reaction of a plurality of granules, especially of different immunocytes, in the same reaction chamber, the reaction chamber is observed by means of the microscope in predefined, different horizontal planes. The observation in the different horizontal planes may be carried out in a predefined chronological sequence. A high-resolution microscopy may be used for this purpose. Especially digital, holographic microscopy or shearography is preferably achieved with the microscope. The microscope may be configured especially for generating a holographic image. Shearography here may be the short name for shearing interferometry and/or laser speckle shearing interferometry. It is a coherently optical measurement method that is known per se. In particular, an LED (LED: Light-Emitting Diode) may be used instead of a laser. Digital holographic microscopy utilizes the principle of holography to generate an image. The blood sample to be tested or the immunocytes to be tested can be illuminated here by means of a light source, especially an LED or a laser. The light scattered in the process may interfere with light of a reference source of the same light source, especially of the same LED or of the same laser. The reference source may be provided here by means of the reference chamber. The interference pattern formed in this process can make the direct and/or optical observation possible. In particular, the interference pattern may be recorded by means of a preferably digital sensor. The microscope preferably makes it possible to determine a quantitative phase contrast.

According to another embodiment, which is also conceivable on its own merit and independently from the present invention, live immunocytes of the blood sample are identified by means of the microscope. Distinction can thus be made between live and dead cells. The identification of live immunocytes can now be carried out in an automated manner. Automated identification of live immunocytes makes it possible to considerably reduce the time and/or cost. Only immunocytes identified as live cells are preferably taken into consideration during the observation and/or the analysis of a reaction of the immunocytes during contacting with the at least one allergen. As a result, errors in the analysis of the observation can be reduced. The fact that an allergic reaction is not observed in a dead immunocyte is especially prevented from being interpreted as a nonexistent allergic sensitization or allergy. A state of stimulation of immunocytes, especially basophilic cells, is preferably determined. The microscope may preferably be configured for this as a quantitative phase contrast microscope. An optical path of the light through at least one immunocyte and/or a light absorption by at least one immunocyte can be measured and/or analyzed. In particular, dead immunocytes can be distinguished from live immunocytes based on a measurement of the optical path or of the path of the light, because dead immunocytes burst on dying and this leads to a change in the optical path or in the path of the light.

According to a variant, a position of granules in immunocytes, a motion of the granules and/or degranulation are observed over an observation time of up to 10 minutes or longer. The observation time is, in particular, in a range of 60 sec to 300 sec. The observation time may be started with the contacting of the blood sample with the at least one allergen or with the introduction of the at least one allergen into the microfluidic chip. A plurality of reaction chambers of a microfluidic chip may be observed consecutively several times at predefined time intervals during the observation time. In particular, a plurality of planes or horizontal planes may be observed several times consecutively at predefined time intervals during the observation time. It is thus unnecessary to observe a single reaction chamber and/or a single plane within a single reaction chamber uninterruptedly over the entire observation time. It may suffice, instead, to make a plurality of observations and/or recordings within the observation time in order to carry out an analysis on the basis of a sequence of observations and/or recordings.

The observation and/or analysis are preferably carried out in an automated manner. The time needed and/or the cost can be reduced hereby. In particular, digital image recording and/or image acquisition is employed to observe a response of the blood sample, especially of the immunocytes, to the contacting with the at least one allergen. It is possible to use, for example, an image processing software for providing and/or analyzing recorded images. A possibly existing allergic sensitization or allergy in respect to different allergens can be tested hereby within a relatively short time. A corresponding allergy test may be carried out in a time of less than 6 hours, less than 3 hours, less than 1 hour or less than 10 minutes.

A process for determining degranulation in cells, especially a process having the features of the process being described here for carrying out an allergy test, is an especially advantageous embodiment, which is also conceivable on its own merit and independently from the present application. Degranulation or the absence of degranulation can be observed here by means of a microscope directly and/or optically. The position and/or a change in the position of granules of the cells being observed can be determined by means of the microscope directly and/or optically. Degranulation is determined, in particular, on the basis of an observation and/or measurement of a quantitative phase contrast. A quantitative phase contrast of at least one cell can be determined or measured here by means of an interferometric measurement of superimposed light. A first part of the superimposed light may pass through a reaction chamber containing the at least one cell and another part of the superimposed light may pass through a reference chamber without cells. The microscope may be configured to generate a holographic image.

Furthermore, a device for carrying out an allergy test with a process according to the present invention is advantageous, the device having a microscope and an at least partially transparent microfluidic chip for the direct and/or optical observation of degranulation and the microscope being configured to generate a holographic image. The microscope may optionally have only relevant parts, especially an objective lens device, a sensor device and/or a lens device, of a usual microscope. An especially compact configuration or design of the device may be able to be obtained hereby. In particular, an allergic reaction or the absence of an allergic reaction can be observed by means of the device.

According to a variant, the microfluidic chip has at least one reaction chamber, and especially a plurality of reaction chambers. At least one, two or more microchannels may open into the reaction chamber. A plurality of reaction chambers may be separated from one another by means of separating elements or walls. The microfluidic chip has, in particular, transparent window surfaces in the area of the at least one reaction chamber. The transparent window surfaces may be arranged on two sides of the microfluidic chip, which sides face away from one another. The transparent window surfaces may be oriented obliquely or at right angles to an optical axis, an optical path and/or a light path of the device and/or of the microscope. The transparent window surfaces are arranged in relation to one another, in particular, such that an optical path, a light path, a light wave and/or an electromagnetic wave can enter the reaction chamber through a first window surface and leave the reaction chamber through a second window surface. A reference chamber is preferably associated with each reaction chamber. The reference chamber may have transparent window surfaces. Transparent window surfaces of the reference chamber are arranged, in particular, on two sides of the microfluidic chip that face away from one another. The transparent window surfaces of the reaction chamber are preferably also the transparent window surfaces of the associated reference chamber. The window surfaces may be formed each by means of a glass layer. A single or individual glass layer may cover one side of the microfluidic chip here.

The at least one reaction chamber and/or a reference chamber preferably has a base or a transparent window surface in the range of about 100 μm×100 μm each on two sides facing away from one another. The base of the at least one reaction chamber and/or of the reference chamber or the transparent window surface in the area of the at least one reaction chamber and/or in the area of the reference chamber is especially smaller than 50,000 m$^2$, smaller than 20,000 μm$^2$ or about 10,000 m$^2$. The at least one reaction chamber and/or the reference chamber have especially a height of less than 1 mm and/or less than 100 μm.

According to another embodiment, the microscope has an, especially digital, holographic microscope or a shearography microscope. The microscope preferably has a quantitative phase contrast microscope. The microfluidic chip is arranged especially between a light source and an objective lens device. The light source may be configured as an LED or a laser. The microfluidic chip may be fastened to a carrying device. The light source, on the one hand, and the objective lens device and/or the microscope, on the other hand, may be arranged, starting from the microfluidic chip, in two areas mutually facing away from one another. Furthermore, the objective lens device may be a part of the microscope and/or be arranged between the microscope and the microfluidic chip. The microscope is preferably connected to a computer. The computer may be configured to display, record, store and/or analyze images and/or data. In particular, automated observation and/or analysis can be carried out by means of a computer.

A microfluidic chip, especially for a device according to the present invention, is especially advantageous and is also conceivable independently as well as on its own merit in respect to the present invention. The microfluidic chip may have electrodes for the electrophoretic and/or dielectrophoretic positioning of cells, especially immunocytes. The cells or immunocytes may be positioned in this connection in at least one reaction chamber of the microfluidic chip. The microfluidic chip may have at least one reference chamber. A respective reference chamber is especially associated with each reaction chamber. In particular, a reference chamber is formed adjacent to the reaction chamber based on a shape and/or orientation of at least one electrode. The electrode, which is especially strand-like, preferably has a deflection and/or an arc to form the at least one reference chamber. A dual function can thus be achieved by means of one electrode. The at least one electrode brings about, on the one hand, a reliable positioning and/or holding of cells or immunocytes in the reaction chamber. At the same time, the at least one reference chamber is formed based on the suitable configuration or shape of the at least one electrode. The electrode guarantees in this connection that no cells or immunocytes will enter the reference chamber, especially after positioning the cells in the reaction chamber. The reference chamber is preferably formed between a first electrode and at least one additional electrode.

Especially advantageous is the use of a process according to the present invention, of a device according to the present invention and/or of a microfluidic chip according to the present invention for carrying out an allergy test. The visualization or the quantitative detection of degranulation represents, in particular, as opposed to prior-art allergy tests, a direct method. As a result, the number of incorrect analyses can be considerably reduced, and the time needed can be considerably reduced, because a corresponding allergic reaction can be observed within a period of a few minutes, especially within 60 sec to 300 sec, in the presence of an allergic sensitivity. Finally, comprehensive tests can be carried out with the known and usual allergens used hitherto by means of a relatively small quantity of blood sample.

The present invention will be explained in more detail below on the basis of the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is a schematic flow chart for a process according to the present invention.

DESCRIPTION OF PREFERRED EMBODIMENTS

Figure 1:
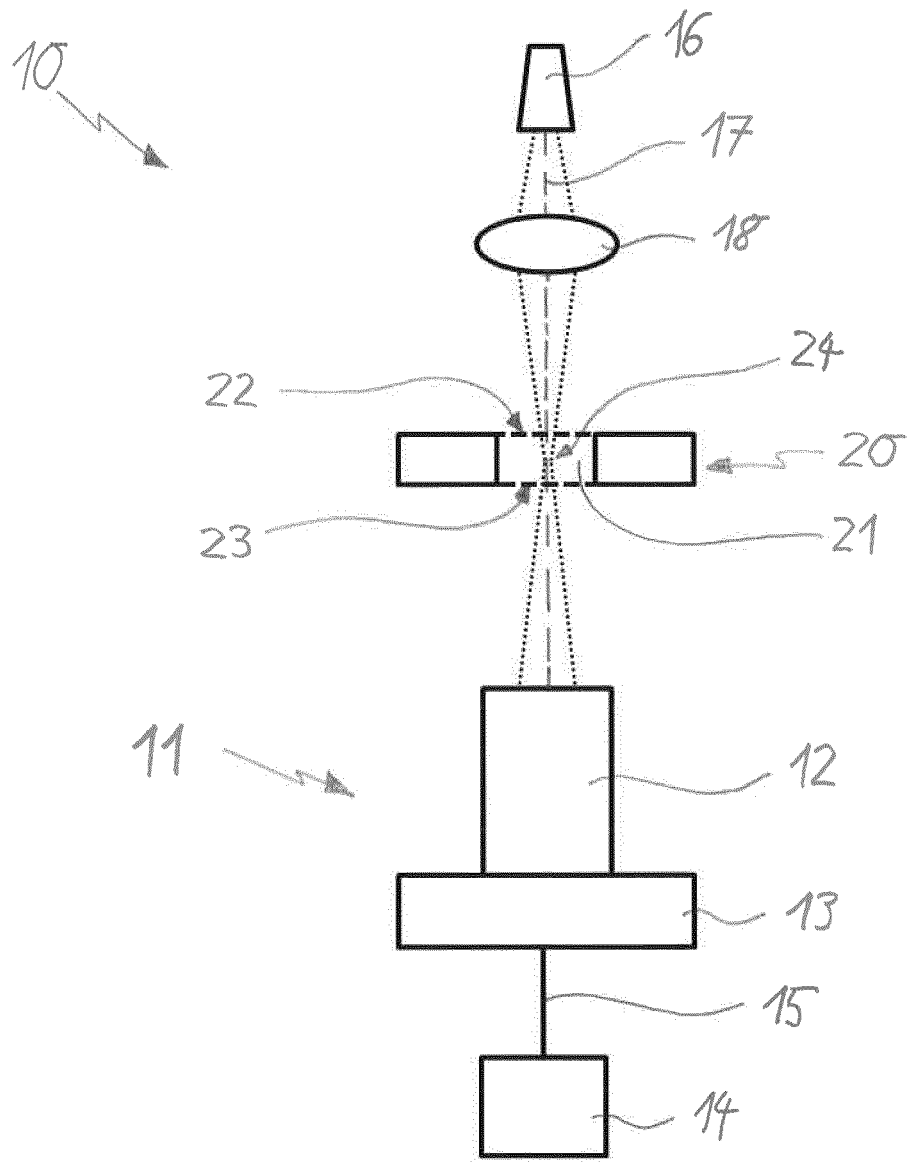
FIG. 1 is a schematic lateral view of a device according to the present invention.

Referring to the drawings, FIG. 1 shows a schematic lateral view of a device 10 according to the present invention. The device 10 has a microscope 11. The microscope 11 is configured in this exemplary embodiment as a digital holographic microscope. The microscope 11 may be configured, in particular, to generate a holographic image. The microscope 11 has, furthermore, an objective lens device 12 and a sensor device 13 in this exemplary embodiment. The sensor device 13 may be configured as a detector and/or as an image sensor, especially a CCD sensor.

The microscope 11 is connected to a computer 14. As a result, data of the microscope 11 or of the sensor device 13 can be transmitted to the computer 14 by means of a data line 15. Furthermore, the microscope 11 can be controlled by means of the computer 14.

The device 10 has a light source 16. The light source 16 is configured as an LED in this exemplary embodiment. As an alternative, the light source 16 may be a laser. The light source 16 is arranged in this schematic view such that an optical axis 17 is oriented in the direction of the microscope 11. The optical axis 17 is shown here as a broken line. Furthermore, a spatial modulator, especially a so-called SLM (Spatial Light Modulator), not shown more specifically here, may be present for the light of the light source 16.

The device 10 has a lens device 18. The lens device is configured as a lens-filter device in this exemplary embodiment. The lens device 18 is configured to focus and/or filter a light beam 19. The light beam 19 is indicated here schematically by means of dotted lines. The lens device 18 may have one or more lenses. Furthermore, the lens device 18 is arranged between the light source 16 and the microscope 11 on the optical axis 17. The lens device 18 can be controlled in this exemplary embodiment to set or change the focus. The lens device 18 may be controlled, for example, by means of the computer 14.

Finally, the device 10 has a microfluidic chip 20. The microfluidic chip 20 may be positioned and/or held by means of a carrying device, which is not shown in more detail here. The microfluidic chip 20 is arranged between the light source 16 and the microscope 11. The microfluidic chip 20 is positioned here on the optical axis 17 between the lens device 18 and the objective lens device 12. The microfluidic chip 20 has an at least partially transparent configuration. As a result, the light beam 19 can be guided, starting from the light source 16, through the microfluidic chip 20 to the microscope 11. As an alternative, the microfluidic chip 20 may be configured such that it is transparent on one side only, in which case the irradiation and the observation or measurement are performed from the same side.

The microfluidic chip 20 has at least one reaction chamber 21. The microfluidic chip 20 has transparent window surfaces 22, 23 at least in the area of the at least one reaction chamber 21. The window surfaces 22, 23 are arranged on two sides of the microfluidic chip 20, which face away from one another. The plane of the microfluidic chip 20 or of the window surfaces 22, 23 is oriented obliquely and in this exemplary embodiment essentially at right angles to the optical axis 17.

A focus 24 of the light beam 19 is positioned within the reaction chamber 21. The position of the focus 24 within the at least one reaction chamber 21 can be changed by means of a suitable control, especially the computer 14. For example, the focus 24 can be shifted essentially in the longitudinal direction of the optical axis 17. As a result, different planes or horizontal planes can be observed within the at least one reaction chamber 21.

Figure 2:
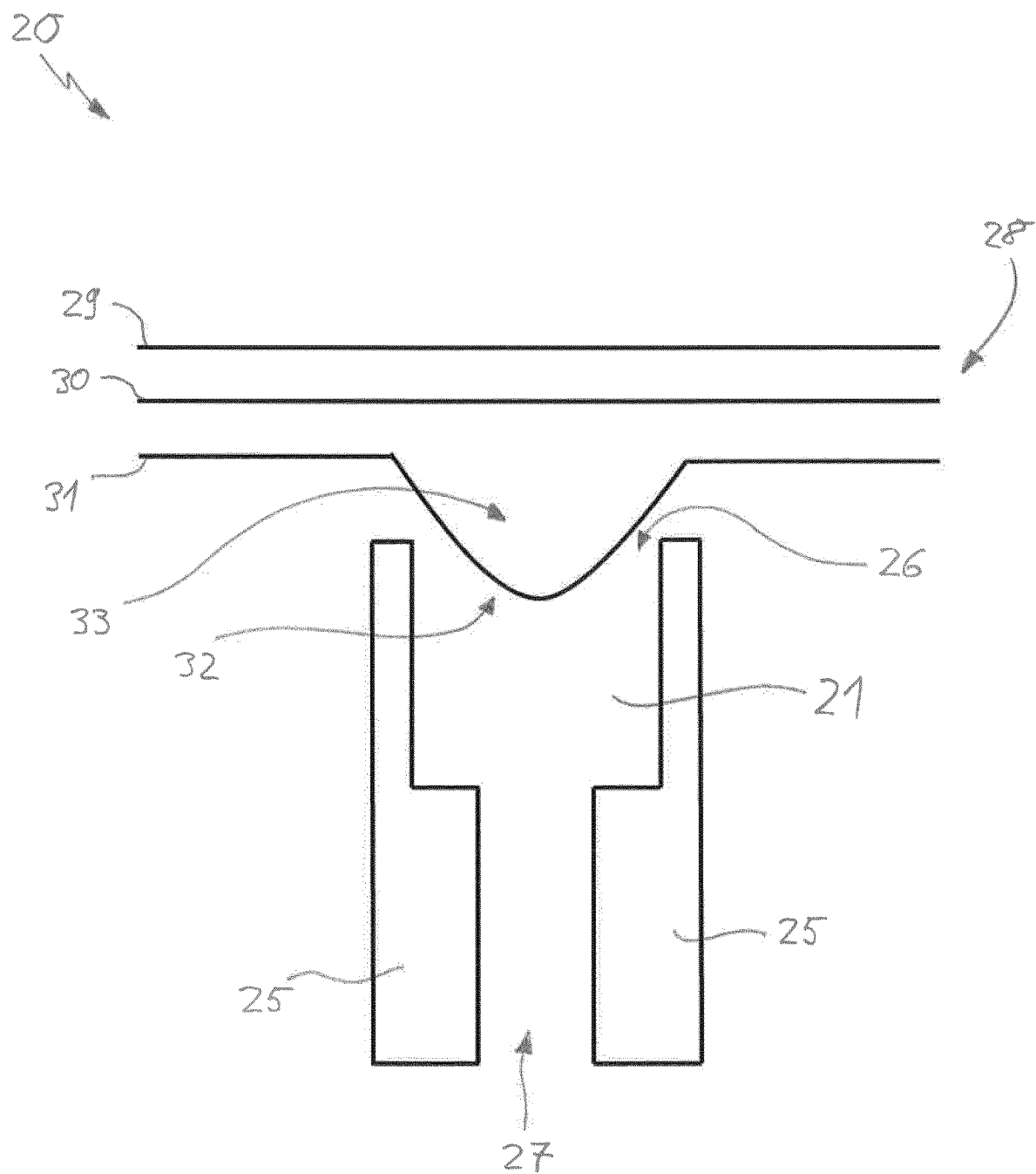
FIG. 2 is a schematic detail top view of a microfluidic chip according to the present invention.

FIG. 2 shows a schematic detail of a microfluidic chip 20 according to the present invention. The schematic detail is shown here as a top view. The microfluidic chip 20 has a plurality of reaction chambers 21, but only a single reaction chamber 21 is shown here. The microfluidic chip 20 has a plurality of separating elements 25. The position and/or size of the at least one reaction chamber 21 can be defined by means of the separating elements 25. The separating elements 25 are used, in particular, to separate a plurality of reaction chambers 21. The separating elements 25 are configured as partitions in this exemplary embodiment.

The reaction chamber 21 has an access opening 26. Cells or immunocytes of a blood sample, which are not shown here in more detail, can enter the reaction chamber 21 by means of the access opening 26. The term blood sample may be used for a direct blood sample or for a serum from a direct blood sample, which serum was mixed or brought into contact with cells of special cell lines.

Furthermore, the microfluidic chip 20 has at least one microchannel 27. Each reaction chamber 21 is connected, in particular, with at least one microchannel 27. At least one allergen, not shown here in more detail, can be guided by means of the microchannel 27 into the reaction chamber 21. The access openings 26 and the microchannel 27 are arranged in this exemplary embodiment on sides of the reaction chamber 21 that face away from one another. Furthermore, both the access opening 26 and the microchannel 27 are configured in this exemplary embodiment by means of two separating elements 25 arranged parallel to one another and mirror-symmetrically to one another.

The microfluidic chip 20 has a dielectrophoretic positioning device 28. The dielectrophoretic positioning device 28 has a plurality of electrodes 29, 30, 31. The electrodes 29, 30, 31 have an essentially strand-like configuration. Furthermore, the electrodes 29, 30, 31 are oriented essentially parallel to one another. The dielectrophoretic positioning device 28 or the electrodes 29, 30, 31 are arranged or configured such that cells or immunocytes can be positioned dielectrophoretically in the at least one reaction chamber 21. The electrode 31 located closest to the reaction chamber 21 has a deflection 32 in the area of the reaction chamber 21 or of the access opening 26. The deflection 32 is formed in the direction of the reaction chamber 21 or of the access opening 26. The deflection 32 is embodied in this exemplary embodiment as a type of bulge of the electrode 31. As an alternative, the deflection 32 may have an essentially C-, U- or V-shaped configuration. The deflection 32 partially protrudes in this exemplary embodiment into the area of the access opening 26. In case of a plurality of reaction chambers 21 arranged next to one another, the electrode arranged closest to the reaction chambers 21 may have a meandering configuration. An arch is formed in this case in the area of the reaction chambers 21 in the direction of the reaction chamber 21 and a respective arch pointing away from the separating elements 25 is formed in areas of the separating elements 25.

Due to the deflection 32, a reference chamber 33 is formed between the electrode 31 having the deflection 32 and the electrode 30 located closest hereto. Due to the dielectrophoretic action of the positioning device 28, it can be achieved that no cells or immunocytes can be positioned within the reference chamber 33 and they can only be positioned in the reaction chamber 21. At the same time, at least one allergen can be guided by means of the microchannel 27 both into the reaction chamber 21 and the reference chamber 33. As an alternative, the at least one allergen can only be guided into the reaction chamber 21 and not into the reference chamber 33.

The reaction chamber 21 and the reference chamber 33 can be observed directly and/or optically by means of window surfaces 22, 23, as is shown in FIG. 1. The reference chamber 33 makes possible the observation of superimposed light, which passes through the reaction chamber 21 and through the reference chamber 33. A first part of the superimposed light can pass through the reaction chamber 21 and another part of the superimposed light can pass through the reference chamber 33. A quantitative phase contrast microscopy is made possible hereby.

FIG. 3 shows a schematic flow chart for a process according to the present invention. The process will be explained below in more detail taking into account the device 10 and the microfluidic chip 20 according to FIGS. 1 and 2.

After a start of the process according to step S10, a blood sample is taken with step S11. For example, a blood sample may be taken from a person or a patient in the usual manner by means of a needle or syringe. However, relatively small quantities of blood are sufficient for the process according to the present invention. In particular, a blood sample quantity of less than 50 mL, less than 20 mL or less than 1 mL is sufficient.

The blood sample is subsequently processed according to step S12. An additive is added to the blood sample within the framework of the processing of the blood sample in this exemplary embodiment in order to prevent clotting of the blood. Furthermore, the percentage of the immunocytes to be tested is increased in the blood sample within the framework of the processing of the blood sample. Red blood cells are removed for this purpose from the blood sample in this exemplary embodiment by means of processes that are known per se. Furthermore, nonrelevant white blood cells may likewise be removed according to processes that are known per se. The basophilic cells are isolated or their percentage is increased in the blood sample in this exemplary embodiment. It is sufficient in this exemplary embodiment to increase the percentage of basophilic cells in the blood sample in a range of 10% to 20%. The blood sample is then suspended or the cells are then suspended in a suitable medium in order to keep the cells alive for a predefined time, especially for up to 24 hours.

The blood sample is subsequently applied to or introduced into a microfluidic chip 20 according to step S13. The microfluidic chip 20 may be configured here such that the blood sample or the immunocytes to be tested are guided into the microfluidic chip 20 by means of capillary forces. As an alternative, the blood sample or the immunocytes may be pumped into the microfluidic chip 20 by means of a suitable device.

Immunocytes are then positioned in at least one reaction chamber 21 according to step S14. The positioning may be carried out here by means of suitably configured cell traps, microchannels or an electrophoretic or dielectrophoretic positioning device 28. A plurality of immunocytes are arranged each time in a reaction chamber 21 by means of the dielectrophoretic positioning device 28 in this exemplary embodiment. Furthermore, immunocytes are guided into a plurality of reaction chambers 21 and are held there by means of the dielectrophoretic positioning device 28.

At least one allergen is subsequently introduced according to step S15. At least one allergen is guided, especially in the liquid form, into the reaction chamber 21 and into the corresponding reference chamber 33 by means of the microchannel 27 in this exemplary embodiment.

An optical monitoring of the immunocytes is carried out according to step S16. The optical monitoring may already be started prior to the introduction of the at least one allergen, together with the introduction of the at least one allergen or immediately after the introduction of the at least one allergen. Optical monitoring is carried out in this exemplary embodiment by means of the microscope 11. The optical monitoring is embodied in this exemplary embodiment as a quantitative phase contrast microscopy. Granules of the immunocytes are observed here directly and/or optically by means of the microscope 11. The observation is carried out, in particular, over a predefined time of 60 sec to 300 sec or longer in order to determine whether degranulation takes place after contacting the immunocytes with the at least one allergen. The microscope 11 may make possible for this a digital image recording or a digital image acquisition. A plurality of immunocytes are observed within the framework of the observation or monitoring performed in different planes or horizontal planes of the at least one reaction chamber 21. The microscope 11 may be configured for this especially for generating a holographic image.

An analysis of the optical observation or monitoring is then carried out according to step S17. If degranulation is observed after contacting the immunocytes with the at least one allergen, this is classified as an allergic reaction. If, by contrast, no observable degranulation takes place, this is considered to be a non-allergic reaction.

The process then ends according to step S18.

While specific embodiments of the invention have been shown and described in detail to illustrate the application of the principles of the invention, it will be understood that the invention may be embodied otherwise without departing from such principles.

The invention claimed is:

1. A process for carrying out an allergy test, the process comprising:

contacting a blood sample with at least one allergen in vitro; and detecting in vitro at least one allergic reaction or an absence of the at least one allergic reaction directly optically by means of a microscope comprising detecting a position of granules of cells by means of the microscope, wherein the cells comprise immunocytes, wherein the immunocytes of the blood sample are arranged in an at least one reaction chamber of a microfluidic chip, the at least one reaction chamber having an at least partially transparent configuration, wherein the granules are detected in a plurality of planes within the at least one reaction chamber, wherein degranulation of the immunocytes of the blood sample is detected with the microscope in case of the at least one allergic reaction, wherein the position of the granules in the immunocytes, a motion of the granules and/or the degranulation is detected within the at least one reaction chamber for an observation time, the observation time being one of about 1 minute to 10 minutes and about 60 seconds to 300 seconds, wherein one of: each of the plurality of planes is different from each other; and each of the planes is a horizontal plane.

2. The process in accordance with claim 1, wherein degranulation of immunocytes, granulocytes, basophilic cells, and/or mast cells, of the blood sample is determined with the microscope in case of an allergic reaction, and an absence of degranulation is classified as a non-allergic reaction and a presence of degranulation is classified as an allergic reaction on the basis of the direct optical observation of the immunocytes on contacting with the at least one allergen.

3. The process in accordance with claim 1, wherein before contacting the blood sample with the at least one allergen, the blood sample is processed to increase a percentage of immunocytes, wherein the percentage of immunocytes in the blood sample is increased to at least 5%, and a percentage of red blood cells and/or of white blood cells different from immunocytes, granulocytes, basophilic cells, basophilic granulocytes and/or mast cells is reduced.

4. The process in accordance with claim 1, wherein the microfluidic chip is used for contacting the blood sample with the at least one allergen, and an at least one reference chamber of the microfluidic chip has an at least partially transparent configuration.

5. The process in accordance with claim 4, wherein at least one allergen is guided into the at least one reaction chamber, and the at least one allergen is especially guided both into the at least one reaction chamber containing the immunocytes and into a reference chamber without immunocytes, and the reference chamber is associated with the at least one reaction chamber.

6. The process in accordance with claim 4, wherein immunocytes of the blood sample are arranged on or in the microfluidic chip by means of a microfluidic cell trap, electrophoresis and/or dielectrophoresis, immunocytes are positioned and/or held by means of electrophoresis and/or dielectrophoresis in at least one reaction chamber, and at least one reference chamber is provided as a chamber free from immunocytes by means of electrophoresis and/or dielectrophoresis.

7. The process in accordance with claim 1, wherein the position and/or a change in the position of granules of immunocytes are determined directly and/or optically by means of the microscope, and an especially digital, holographic microscopy, shearography and/or a quantitative phase contrast microscopy are carried out with the microscope.

8. The process in accordance with claim 1, wherein live immunocytes of the blood sample are identified by means of the microscope, the identification of live immunocytes being carried out in an automated manner, and only immunocytes identified as live immunocytes are taken into account during the observation and/or the analysis of a reaction of the immunocytes on contacting the immunocytes with the at least one allergen.

9. The process in accordance with claim 1, wherein a position of granules in immunocytes, a motion of the granules and/or degranulation are detected over the observation time, the observation time being started with the contacting of the blood sample with the at least one allergen, and a plurality of reaction chambers of a microfluidic chip are observed several times consecutively at predefined time intervals during the observation time.

10. The process in accordance with claim 1, wherein the observation and/or analysis are carried out in an automated manner, comprising using a digital image recording to detect a reaction of the blood sample upon contacting the blood sample with the at least one allergen and/or using an image processing software to provide and/or analyze recorded images.

11. The process for determining degranulation in cells, especially with a process in accordance with claim 1, in which a blood sample is taken, and in which the blood sample is contacted in vitro with at least one reaction partner, wherein degranulation or the absence of degranulation is detected directly and/or optically by means of a microscope, the determination of the degranulation being carried out on the basis of an observation and/or measurement of a quantitative phase contrast.

12. The process in accordance with claim 1, wherein the microscope is configured to generate a holographic image.

13. The process in accordance with claim 12, wherein the microfluidic chip comprises transparent window surfaces in an area of the at least one reaction chamber on two sides facing away from one another, and a reference chamber, with transparent window surfaces associated with the at least one reaction chamber on two sides facing away from one another, the device further comprising a microfluidic cell trap or electrodes for electrophoretic and/or dielectrophoretic positioning of immunocytes in the at least one reaction chamber, wherein no immunocytes are positioned within the reference chamber or the at least one allergen cannot be directed into the reference chamber.

14. The process in accordance with claim 13, wherein the at least one reaction chamber and/or a reference chamber have a base or a respective transparent window surface of 100 µm×100 µm on the two sides facing away from one another, and the at least one reaction chamber and/or the reference chamber have a height of less than 1 mm.

15. The process in accordance with claim 14, wherein:
the microscope comprises a digital, holographic microscope, a shearography microscope and/or a phase contrast microscope;
the microfluidic chip is arranged between a light source and an objective lens device; and
the microscope is connected to a computer for viewing, recording and/or analyzing images and/or data.

16. A process for carrying out an allergy test, the process comprising:
contacting the blood sample with at least one allergen in vitro; and determining in vitro at least one allergic reaction or an absence of the at least one allergic reaction by monitoring a position of granules of cells in a plurality of planes within an at least one reaction chamber of a microfluidic chip during an observation period via a microscope, each of the planes being different from one another and each of the planes being a horizontal plane, the cells comprising immunocytes, wherein the immunocytes of the blood sample are arranged in the at least one reaction chamber of the microfluidic chip, the at least one reaction chamber having an at least partially transparent configuration, the observation time being one of about 1 minute to 10 minutes and about 60 seconds to 300 seconds, wherein the at least one allergic reaction is determined when a degranulation of the immunocytes of the blood sample is detected and the absence of the at least one allergic reaction is determined when no degranulation of the immunocytes of the blood sample is detected.

17. The process in accordance with claim 16, further comprising providing a device comprising the microscope and the at least partially transparent microfluidic chip for the direct and/or optical observation of an allergic reaction or for observing the absence of an allergic reaction, wherein the microscope is configured to generate a holographic image, wherein the microfluidic chip is used for the step of contacting the blood sample and the microscope is used for the step of detecting.

18. The process in accordance with claim 17, wherein the microfluidic chip comprises transparent window surfaces in an area of the at least one reaction chamber on two sides facing away from one another, and a reference chamber, with transparent window surfaces associated with the at least one reaction chamber on two sides facing away from one another, the device further comprising a microfluidic cell trap or electrodes for electrophoretic and/or dielectrophoretic positioning of immunocytes in the at least one reaction chamber, wherein no immunocytes are positioned within the reference chamber or the at least one allergen cannot be directed into the reference chamber.

19. The process in accordance with claim 18, wherein the at least one reaction chamber and/or a reference chamber have a base or a respective transparent window surface of 100 μm×100 μm on the two sides facing away from one another, and the at least one reaction chamber and/or the reference chamber have a height of less than 1 mm.

20. The process in accordance with claim 19, wherein:
the microscope comprises a digital, holographic microscope, a shearography microscope and/or a phase contrast microscope;
the microfluidic chip is arranged between a light source and an objective lens device; and
the microscope is connected to a computer for viewing, recording and/or analyzing images and/or data.

* * * * *